(12) United States Patent
Wincheski et al.

(10) Patent No.: US 8,164,328 B2
(45) Date of Patent: Apr. 24, 2012

(54) EDDY CURRENT SYSTEM AND METHOD FOR CRACK DETECTION

(75) Inventors: Russell A. Wincheski, Williamsburg, VA (US); John W. Simpson, Tabb, VA (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 193 days.

(21) Appl. No.: 12/493,573

(22) Filed: Jun. 29, 2009

(65) Prior Publication Data

US 2010/0079157 A1 Apr. 1, 2010

Related U.S. Application Data

(60) Provisional application No. 61/077,255, filed on Jul. 1, 2008.

(51) Int. Cl.
*G01N 27/82* (2006.01)

(52) U.S. Cl. ........ 324/240; 324/220; 324/225; 324/222; 324/337; 324/338; 324/339; 324/341; 324/342; 324/755.01

(58) Field of Classification Search .................. 324/244, 324/225, 237–242, 220, 755.01
See application file for complete search history.

(56) References Cited

U.S. PATENT DOCUMENTS

| | | | | |
|---|---|---|---|---|
| 5,237,271 A | * | 8/1993 | Hedengren | 324/232 |
| 6,037,768 A | * | 3/2000 | Moulder et al. | 324/225 |
| 2004/0178790 A1 | * | 9/2004 | Gifford et al. | 324/242 |
| 2004/0257072 A1 | * | 12/2004 | Samson | 324/242 |

OTHER PUBLICATIONS

Russell A. Wincheski, et al., "Development of Eddy Current Techniques for the Detection of Stress Corrosion Cracking in Space Shuttle Primary Reaction Control Thrusters, NASA/TP-2007-214878, Jun. 2007."
Russell A. Wincheski et al, "Development of Eddy Current Techniques for the Detection of Cracking in Space Shuttle Primary Reaction Control Thrusters, Review of Progress in Quantitative NDE, Jul. 30-Aug. 4, 2006."
Russell A. Wincheski, "Validation Test Results for Orthogonal Probe Eddy Current Thruster Inspection Systems, NASA/TM-2007-215087, Nov. 2007."

* cited by examiner

*Primary Examiner* — Huy Q Phan
*Assistant Examiner* — Son Le
(74) *Attorney, Agent, or Firm* — Andrea Z. Warmbier; Robin W. Edwards (57) ABSTRACT

An eddy current system and method enables detection of sub-surface damage in a cylindrical object. The invention incorporates a dual frequency, orthogonally wound eddy current probe mounted on a stepper motor-controlled scanning system. The system is designed to inspect for outer surface damage from the interior of the cylindrical object.

16 Claims, 7 Drawing Sheets

EDDY CURRENT SYSTEM AND METHOD FOR CRACK DETECTION

ORIGIN OF THE INVENTION

Pursuant to 35 U.S.C. §119, the benefit of priority from provisional application 61/077,255, with a filing date of Jul. 1, 2008, is claimed for this non-provisional application, and the specification thereof is incorporated in its entirety herein by reference.

This invention was made in part by an employee of the United States Government and may be manufactured and used by or for the Government of the United States of America for governmental purposes without the payment of any royalties thereon or therefor.

FIELD OF THE INVENTION

The present invention relates generally to non-destructive testing, and, more particularly, relates to non-destructive testing using eddy currents.

BACKGROUND

The Space Shuttle Reaction Control System (RCS) provides thrust to the vehicle for attitude and translational maneuvers during flight using both forward and aft RCS thrusters. The reusable Primary RCS (PRCS) thrusters are designed for a minimum of 100 missions, with fourteen forward and twenty-four aft PRCS thrusters on the orbiter providing redundancy to the system. A discovery of stress corrosion cracking in the PRCS thrusters has been identified as a potential failure mechanism of the critical flight hardware and has triggered an extensive non-destructive evaluation (NDE) effort to identify techniques capable of detecting potential damage throughout the thruster inventory. Over the life of the shuttle program, cracking in the relief radius area of seven thrusters has been isolated. Due to unknown variables including crack growth rates, failure modes, and the population of potentially compromised thrusters within the shuttle fleet, it is desirable to develop a system and method for detecting such damage. As the outer surface of the thruster is inaccessible without extensive disassembly, it is desirable to enable on-vehicle or routine depot level inspection of thrusters for relief radius stress corrosion cracking.

SUMMARY OF THE INVENTION

An eddy current system and method enables detection of deep relief radius cracks in a cylindrical object. The technique incorporates a dual frequency, orthogonally wound eddy current probe mounted on a stepper motor-controlled scanning system. The system is designed to inspect for outer surface damage from the interior of the cylindrical object. Extensive testing results have shown that flaws extending to a distance equal to or less than one-third of the inside diameter of the cylinder (ID/3) from the inner surface can be detected.

In one embodiment of the invention, a system for detecting damage below a surface of a cylindrical object comprises an eddy current probe, a scanning mechanism, and a dual frequency eddy current instrument. The eddy current probe comprises first and second eddy current coils which are orthogonal to each other and mounted to the scanning mechanism. The scanning mechanism, by way of a stepper motor, moves the eddy current probe in relation to the surface to be scanned. The dual frequency eddy current instrument is configured for applying a current to the eddy current probe and measuring a resulting impedance as the eddy current probe is moved in relation to the surface. The dual frequency eddy current instrument either (1) concurrently applies a first current having a first frequency and a second current having a second frequency to the eddy current probe as the eddy current probe is moved in relation to the surface, or (2) alternatively applies a first current having a first frequency and a second current having a second frequency to the eddy current probe as the eddy current probe is moved in relation to the surface. The first frequency is selected to penetrate the surface to a depth greater than or equal to a desired flaw detection depth, and the second frequency is selected to isolate a probe wobble and a surface effect. The second frequency is at least twice that of the first frequency. The first and second eddy current coils are mounted to the scanning mechanism such that the first eddy current coil is aligned substantially with a circumferential direction of the surface as the first and second eddy current coils are moved in relation to the surface, and such that the second eddy current coil is aligned substantially parallel to a longitudinal axis of the object as the first and second eddy current coils are moved in relation to the surface.

In one embodiment, the first frequency is between about 10 kilohertz and about 15 kilohertz, and the second frequency is between about 90 kilohertz and about 110 kilohertz.

The system may further comprise a display element for displaying the resulting impedance. The display element displays the resulting impedance at the first frequency, at the second frequency, and at a difference between the first and second frequencies.

The system may further comprise a processing element configured for performing a curve fit of the measured impedance to a predefined function known to represent the measured impedance for an undamaged object. The predefined function is determined through experimental and/or simulation results and has a minimum number of fitting parameters. The processing element may be further configured for calculating and monitoring an error between a best mathematical fit of the predefined function and the measured impedance as a determination of damage in the object.

The scanning mechanism may be further configured for varying a distance between the eddy current probe and the surface. In such an embodiment, the dual frequency eddy current instrument is further configured for rotating the measured impedance such that changes in the impedance caused by motion of the eddy current probe radially toward and away from the surface is along a predefined axis for both the first and second frequencies.

In addition to the system for detecting damage below a surface of a cylindrical object, as described above, other aspects of the present invention are directed to corresponding methods for detecting damage below a surface of a cylindrical object.

BRIEF DESCRIPTION OF THE DRAWINGS

Having thus described the invention in general terms, reference will now be made to the accompanying drawings, which are not necessarily drawn to scale, and wherein:

DETAILED DESCRIPTION

Figure 1:
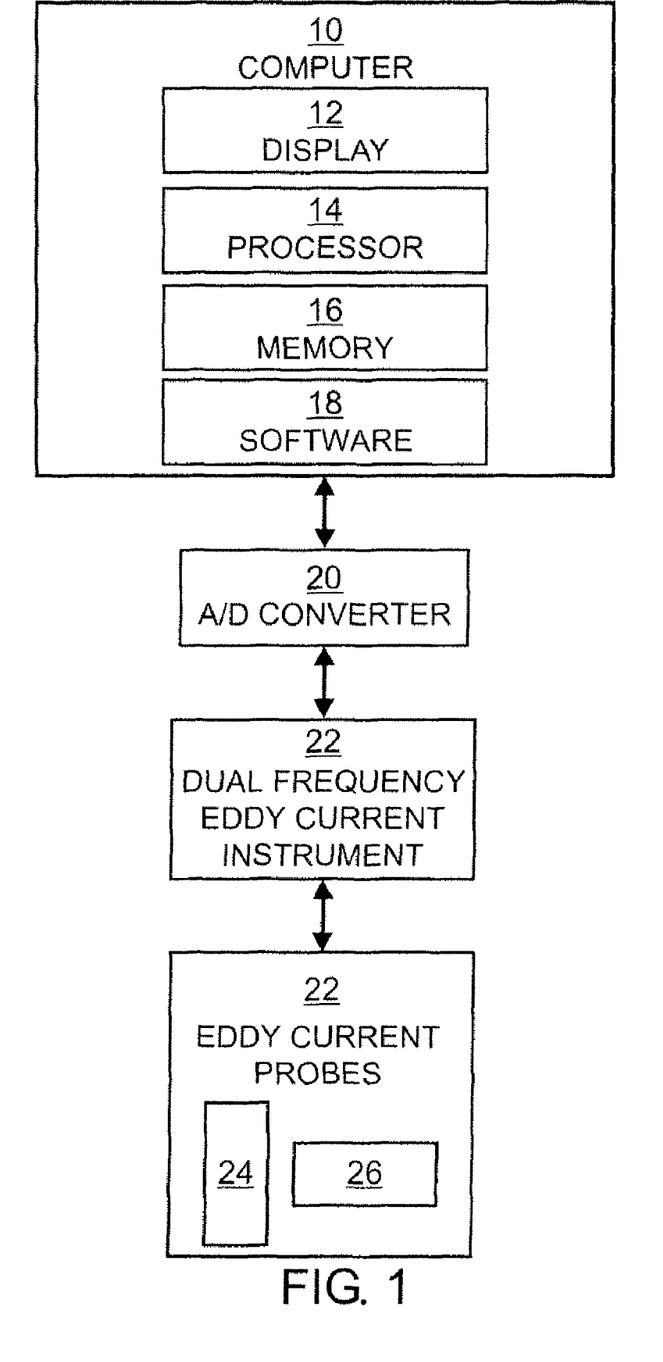
FIG. 1 is a block diagram of a system for detecting sub-surface damage, in accordance with embodiments of the present invention.

FIG. 1 is a block diagram of a system for detecting sub-surface damage (herein termed an "eddy current inspection system"), in accordance with embodiments of the present invention. The eddy current inspection system of FIG. 1 comprises a computer 10, an analog to digital converter 20, a dual frequency eddy current instrument 22, and an eddy current probe 23. The eddy current probe 23 comprises two eddy current coils 24, 26. The computer 10 comprises a display 12, a processor 14, memory 16, and software 18. The dual frequency eddy current instrument 22 controls the two eddy current coils 24, 26 (as described in more detail below) to induce an eddy current and measures the resulting impedance. The signal from the eddy current instrument 22 is fed, via the A/D converter 20, to the computer 10. The software 18, executed by the processor 14, analyzes the resulting impedance (as described in more detail below). Importantly, the two eddy current coils 24, 26 are arranged orthogonally to each other.

Figure 2:
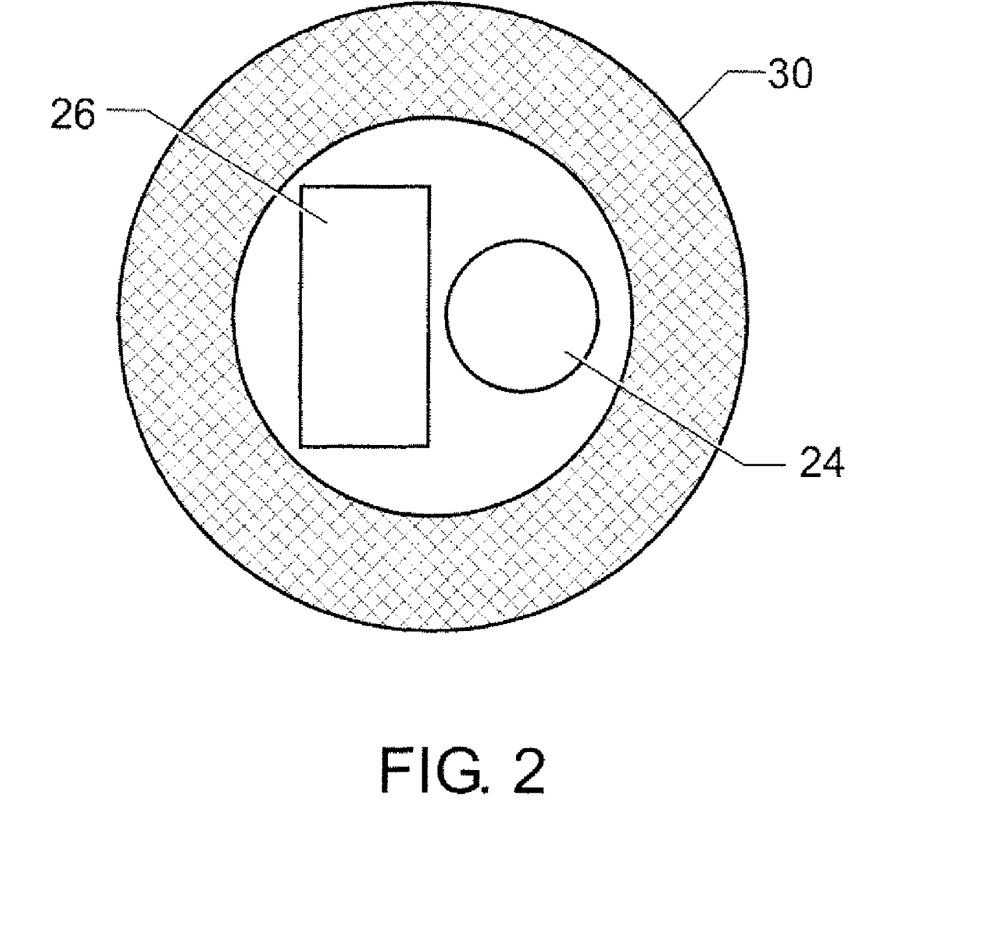
FIG. 2 is a top view conceptual diagram of the system of FIG. 1, in accordance with embodiments of the present invention.

FIG. 2 displays a top-view conceptual diagram of the eddy current inspection system deployed to inspect a cylindrical object 30, in accordance with embodiments of the present invention. The system is able to detect sub-surface damage to the object (i.e., damage within the cross-hatched area). Matched eddy current coils 24, 26 are arranged orthogonally to each other. One inspection coil 26 is arranged with its axis along the circumferential direction of the object. This orientation enables a relatively deep field penetration with a small diameter coil that is able to fit into small spaces, such as the acoustic cavity of a space shuttle thruster, and induces current in a direction that will have a strong interaction with cracking originating in the exterior surface (e.g., along the relief radius of a thruster) and growing in a circumferential direction toward interior of the surface (e.g., toward the acoustic cavity of a thruster). The second coil is arranged with its axis parallel with the axis of the cylindrical object. This second coil is designed to provide a local reference for the inspection coil while minimally interacting with circumferential damage in the part. However, the axis of the first coil along the circumferential direction of the object does not intersect with the axis of the second coil that is substantially parallel with the cylindrical object. For clarity and simplicity, some components of the system that are illustrated in FIG. 1 (the computer 10, A/D converter 20, and dual frequency eddy current instrument 22) are omitted from FIG. 2.

In addition to moving the probe longitudinally through the inside of the object, the probe may be rotated about the center of the two coils to scan in all directions.

Advantageously, embodiments of the invention are able to detect relatively deeply buried defects in cylindrical objects having a small inside diameter, such as the object illustrated in FIG. 2. In such structures, the coil size must be small. This typically reduces the inspection depth of the eddy current technique. The coil configuration (size and orientation) of the embodiments of the present invention greatly improves the detection of 'circumferential' outside diameter cracking in these structures.

Figure 3:
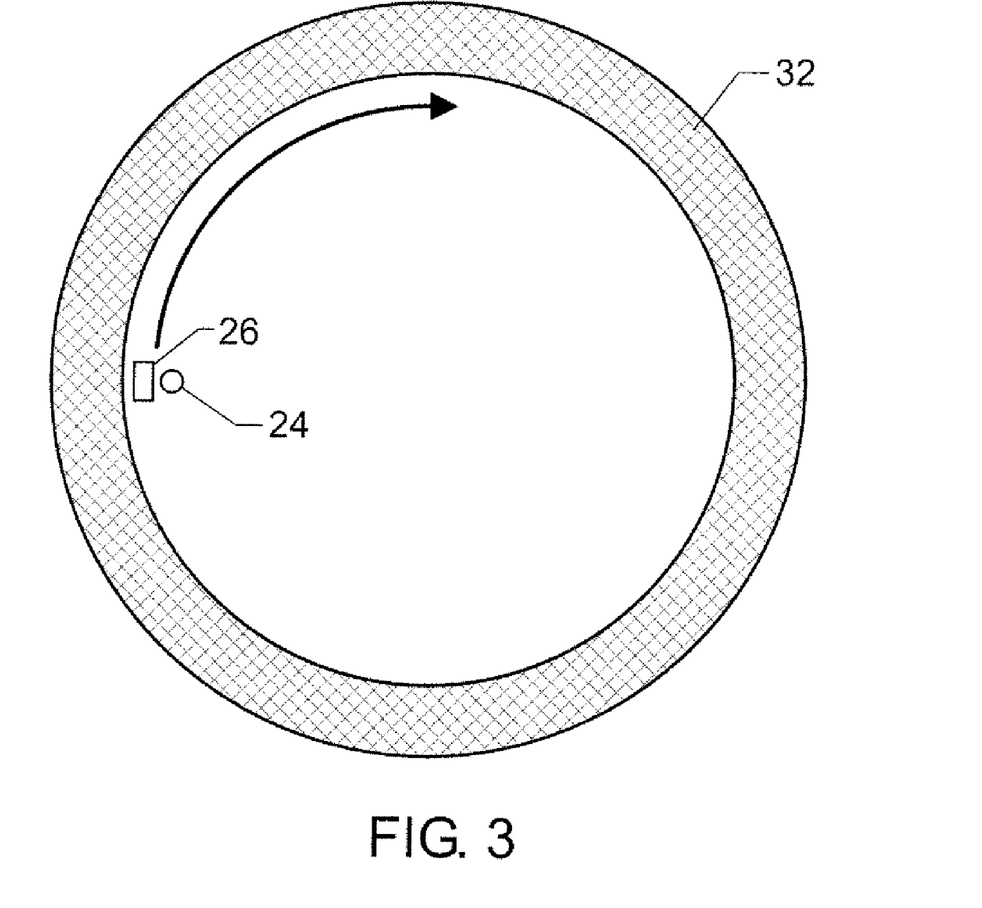
FIG. 3 is a top view conceptual diagram of the system of FIG. 1, in accordance with alternative embodiments of the present invention.

FIG. 3 displays a top-view conceptual diagram of the eddy current inspection system deployed to inspect a cylindrical object 32, in accordance with alternative embodiments of the present invention. While the advantages of using the present invention to detect defects in cylindrical objects having a small inside diameter is discussed above, embodiments of the present invention may be used to detect defects in cylindrical objects having a relatively large inside diameter as illustrated in FIG. 3. In such an embodiment, the coils may be moved along the inner circumference (as illustrated by the arrow in FIG. 3) to scan the entire inside surface. While the coils are moved, the orientation of the probe relative to the inside surface should be maintained.

Figure 4:
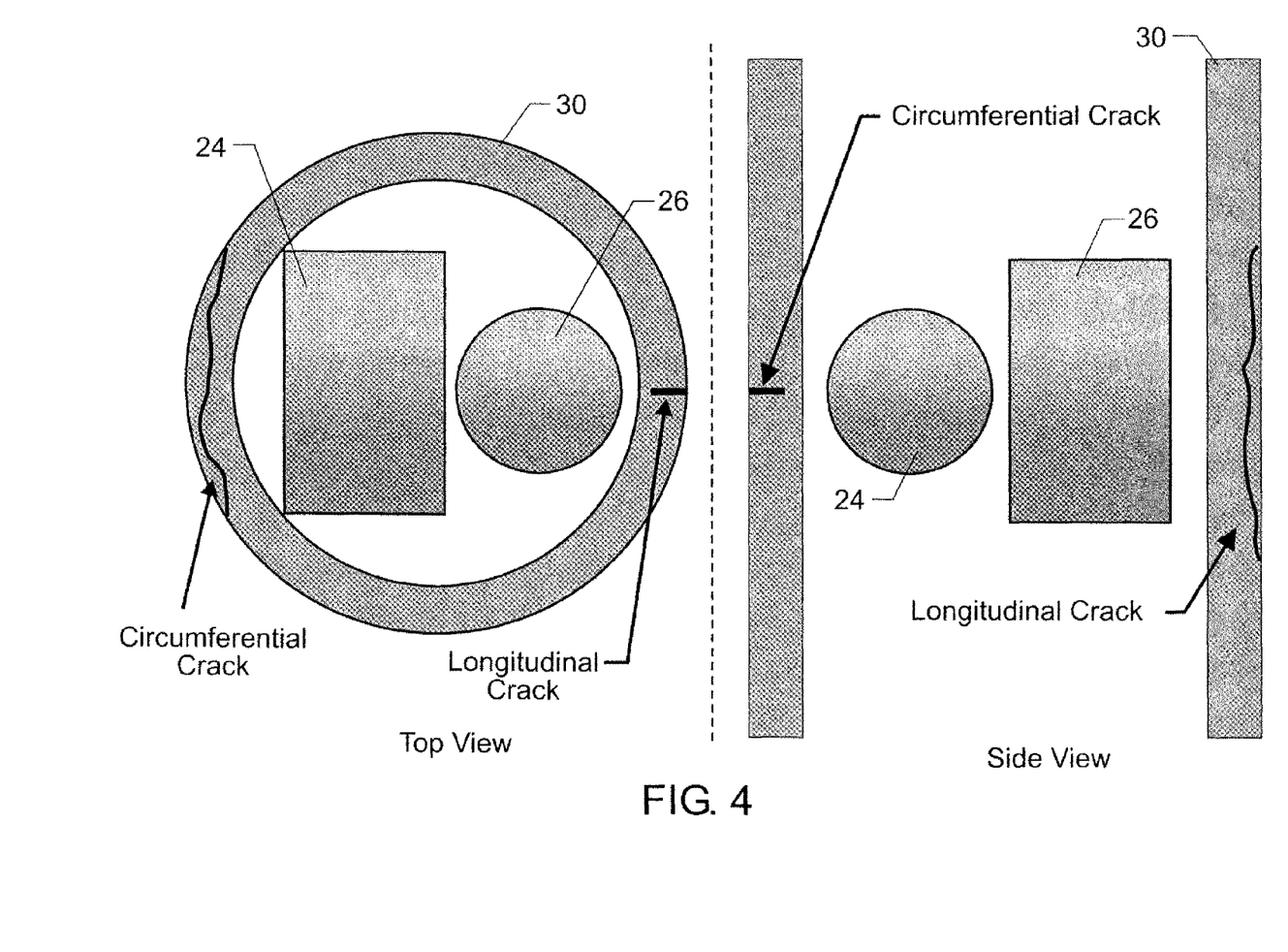
FIG. 4 is a top and side view conceptual diagram of the arrangement of FIG. 2, in accordance with embodiments of the present invention.

FIG. 4 is a top and side view conceptual diagram of the arrangement of FIG. 2, in accordance with embodiments of the present invention. Circumferential and longitudinal cracks in the cylinder are illustrated in FIG. 4. An important aspect of arranging the coils orthogonally is to preferentially detect a given type of flaw with one coil while the second, reference coil, minimally interacts with the defects. Because of the induced current direction in the cylinder wall, the circumferential coil will strongly interact with circumferential cracks. The impedance of the axial coil however, with induced current parallel to the crack direction, will be minimally impacted. In the case of the space shuttle thrusters, circumferential cracking was the concern that was desired to be detected. Therefore, the circumferential coil was considered the detecting coil and was balanced by the axial coil. For detection of longitudinal cracking, the roles of the two coils would be reversed, with the axial coil sensitive to the damage and the longitudinal coil acting as a local reference which minimally interacts with the flaw.

Figure 5:
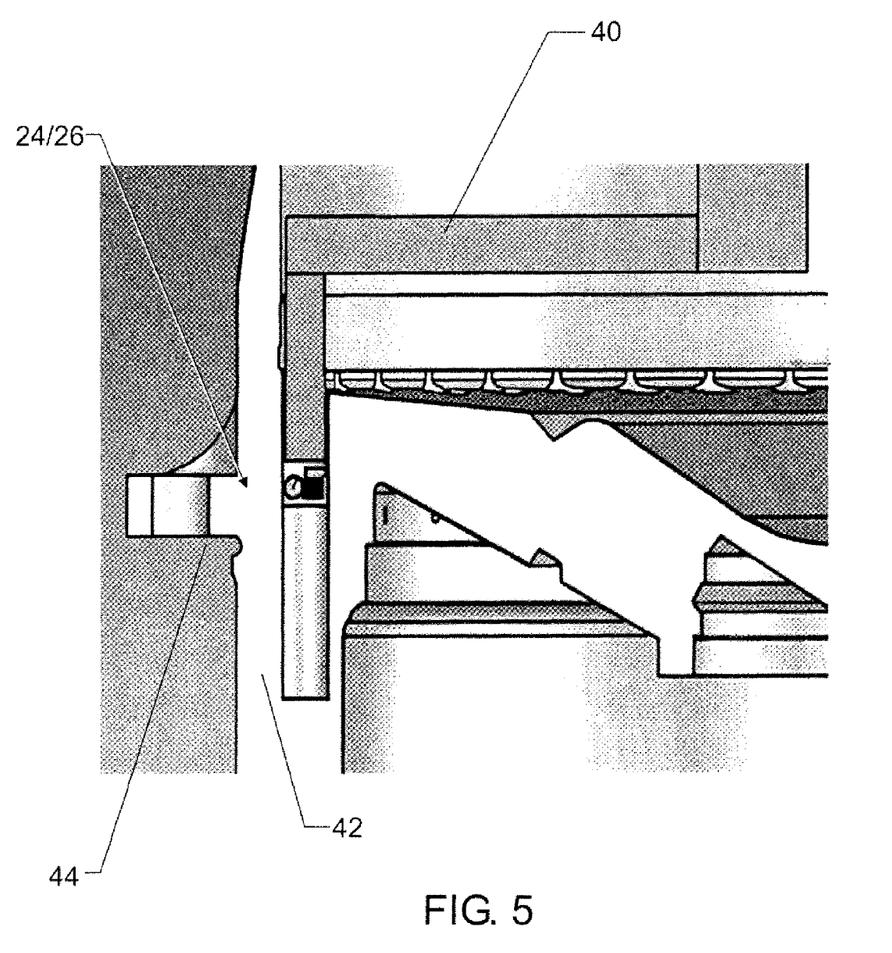
FIG. 5 is a conceptual diagram of the system of FIG. 1 in use in a Space Shuttle Reaction Control System thruster, in accordance with embodiments of the present invention.

FIG. 5 is a conceptual diagram of the eddy current inspection system deployed to inspect a Space Shuttle Reaction Control System thruster, in accordance with embodiments of the present invention. The system of FIG. 5 is able to detect sub-surface damage to the thruster (i.e., damage between the acoustic cavity 42 and the relief radius 44). As in FIG. 2, the deployment of the system illustrated in FIG. 5 comprises matched eddy current coils 24, 26 that are arranged orthogonally to each other (although the eddy current coils are not individually labeled in FIG. 5). One inspection coil is arranged with its axis along the circumferential direction of the thruster. This orientation enables a relatively deep field penetration with a small diameter coil that is able to fit into the acoustic cavity, and induces current in a direction that will have a strong interaction with cracking originating along the relief radius of the thruster and growing in a circumferential direction toward the acoustic cavity. The second coil is arranged with its axis parallel with the axis of the acoustic cavity. This second coil is designed to provide a local reference for the inspection coil while minimally interacting with damage originating at the acoustic cavity. The probe is mounted on a sensor deployment tool 40 (which may also be termed a scanning mechanism). The sensor deployment tool 40 moves the probe into the acoustic cavity and along the surface to be scanned. The movement of the sensor deployment tool 40 may be accomplished using a stepper motor (not illustrated). As in FIG. 2, some components of the system that are illustrated in FIG. 1 (the computer 10, A/D converter 20, and dual frequency eddy current instrument 22) are omitted from FIG. 5.

The dual frequency eddy current instrument 22 of FIG. 1 applies a current to the eddy current probe 23 and measures a resulting impedance as the eddy current probe is moved in relation to the surface being scanned. The dual frequency eddy current instrument may either (1) concurrently apply a first current having a first frequency and a second current having a second frequency to the eddy current probe as the eddy current probe is moved in relation to the surface; or (2) alternatively apply a first current having a first frequency and a second current having a second frequency to the eddy current probe as the eddy current probes is moved in relation to the surface. The first frequency is selected to penetrate the surface to a depth greater than or equal to the desired flaw detection depth, and the second frequency is selected to isolate the probe wobble and the surface effect. The second frequency is typically at least twice that of the first frequency. For example, the first frequency may be between about 10 kilohertz and about 15 kilohertz, and the second frequency may be between about 90 kilohertz (kHz) and about 110 kHz.

The resulting impedance is displayed on the display element 12 of FIG. 1. The resulting impedance is typically displayed at the first frequency, at the second frequency, and at the difference between the first and second frequencies.

In order to interrogate beneath the surface of the acoustic cavity toward the relief radius, a low frequency excitation is required. An estimate of the required operating frequency can be found using the skin depth equation, $$\delta = 1/\sqrt{\pi f \mu \sigma} \quad (1)$$

with $f$=excitation frequency, $\mu$=permeability, and $\sigma$=electrical conductivity. PRCS thrusters are fabricated from columbium (also termed niobium) with nominal values of $\sigma \approx 6.7 \times 10^6$ 1/(ohm-m) and $\mu$=permeability of free space=$4\pi \times 10^{-7}$ Weber/(amp-m). A frequency $f$=12 kilohertz (kHz) then gives a skin depth $\delta \approx 1.8 \times 10^{-3}$ m, or approximately 0.070 inches. The developed inspection procedure incorporates a dual frequency excitation, with the lower frequency enabling deep penetration into the part and the upper frequency helping to mix out responses from surface features such as lift-off and roughness of the acoustic cavity wall. Based upon the calculated skin depth and experimental data, 12 kHz and 100 kHz where chosen as the first and second operating frequencies for the inspection of the PRCS thrusters.

Initial testing of one embodiment of such a system to detect damage in a PRCS thruster performed with the sensor design shown and described above found a good sensitivity to nearly through-wall flaws, but damage that had not progressed to within approximately 0.020"-0.040" of the acoustic cavity was difficult to detect due to the complex geometry of the part. The presence of varying material thickness, fuel passageways, and a potentially rough surface of the acoustic cavities was further complicated by the need to deploy the probe through the injector nozzle, past a narrow throat, and into the acoustic cavity for inspection. To minimize the combined effects of these attributes, a stepper motor controlled scanning system was incorporated into the inspection system. The stepper motor scanning system is deployed in the reaction chamber and rests on the face of the thruster. Once positioned, a pre-programmed scan of the sensor through the area of interest may be performed. The use of the stepper motor scanning system significantly reduces lift-off effects associated with probe tilt and wobble, which are extremely difficult to control under hand scanning. In addition, the stepper motor scanner provides for indexed scanning such that eddy current response data can be plotted directly against location of the probe within the acoustic cavity. Probe responses associated with edge effects and varying wall thickness throughout the scan region can then be directly accounted for and filtered out, greatly enhancing the flaw detectability of the system.

The eddy current coils may be mounted in a probe housing that is attached to the stepper motor. In addition to the eddy current sensor, the probe housing may hold a second, spare, scanning leg. Two other fixed legs may be attached to the scanning system to provide mechanical stability during scanning. When the scanner is positioned within a thruster, the four legs are typically spaced to fit into adjacent acoustic cavities. After receiving a trigger signal, the stepper motor pulls the probe housing (along with the eddy current sensor and spare scanning leg) away from the thruster face, moving the eddy current sensor through the region of interest. Immediately after withdrawing the probe, the stepper motor reverses, thereby moving the sensor once more through the region of interest and back to its start position.

Referring to FIG. 1, the system control and data processing software 18, stored in memory 16 and executed by processor 14, initiates a scan sequence by sending a trigger signal to the stepper motor. Analog output data from the eddy current instrument are then acquired by the computer as the sensor scans partially out of and then back into the acoustic cavity. After the scan completes, the acquired data at 12 kHz, 100 kHz, and frequency mix (calculated as the difference between the 12 kHz and 100 kHz responses) are displayed on display element 12. Nearly through-wall flaws are typically clearly detected in the low frequency and mix signals, with a slight indication of the flaw typically apparent even at 100 kHz. User controls may be provided to enable the plotting of data over any region within the complete scan range, as well as of data acquired during the outgoing or ingoing scan of the probe. Controls may also be present to adjust the mix signal parameters for data analysis on the selected portion of the scan data. A micrograph of a stress corrosion-cracking site dissected from a PRCS thruster may be displayed. The typical crack profile displayed in the micrograph is useful for interpreting the eddy current response in relationship to potential damage in the hardware.

An "Indication Strength" may also be displayed. This value is calculated by fitting the eddy current response to the anticipated profile for the sensor scanned through an unflawed acoustic cavity region. Due to the edge effect as the probe nears the acoustic cavity opening, a sharp increase in the low frequency signal level is typically seen in this region. As the sensor moves into the cavity, a minimum in the low frequency vertical response is typically detected, most likely due to increasing wall thickness in this area. As the probe passes deeper into the cavity, an increase followed by a final slight decrease in the probe output is detected.

Figure 6:
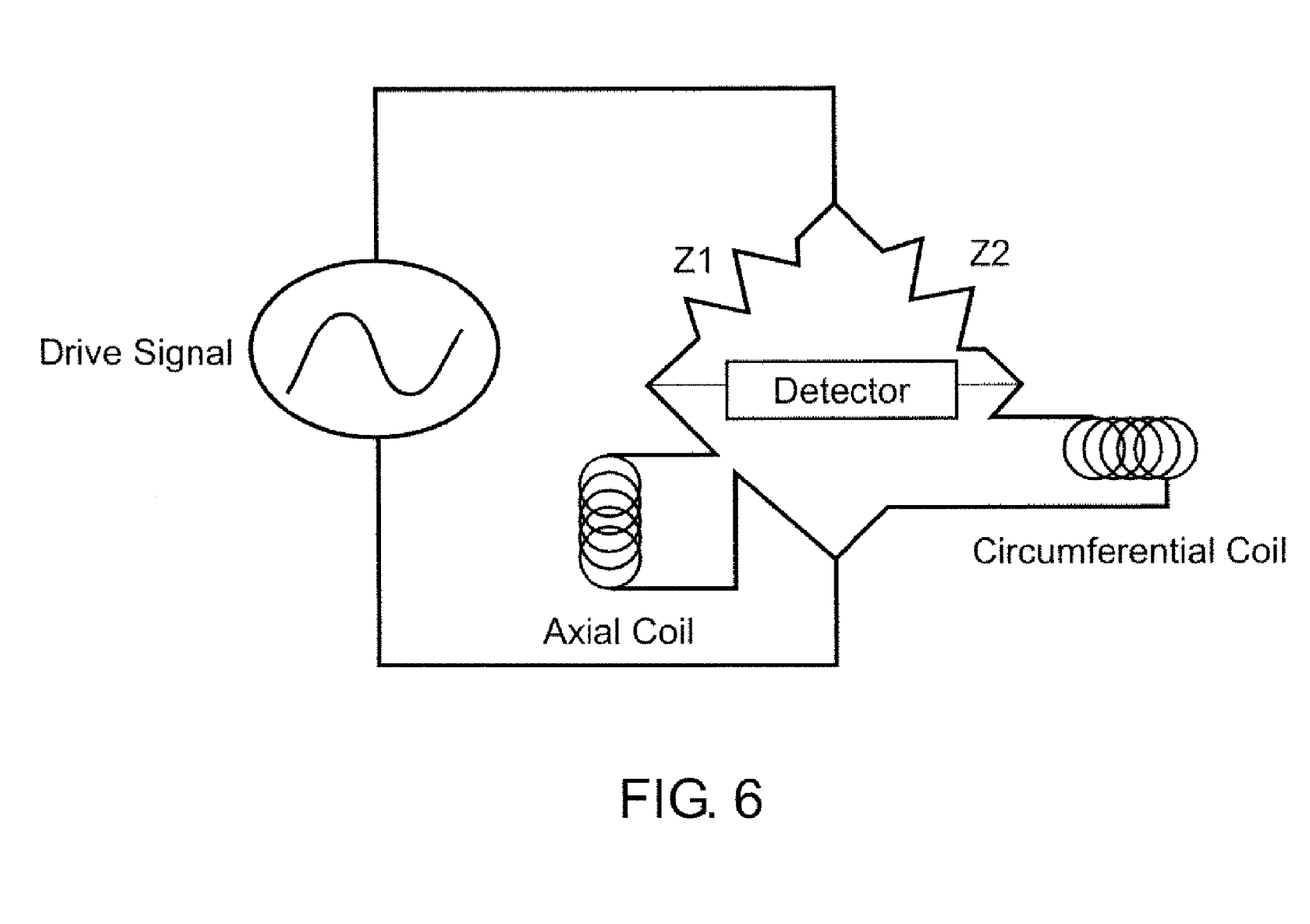
FIG. 6 is a simplified circuit diagram of the system of FIG. 1, in accordance with embodiments of the present invention.

FIG. 6 is a simplified circuit diagram of an eddy current inspection system in accordance with embodiments of the present invention. The system uses a bridge type circuit. Z1 and Z2 are impedance circuit elements internal to the eddy current instrument which are adjusted to balance the bridge before a data set is acquired. The eddy current probe comprises the two coils (i.e., the axial and circumferential coils) on the remaining two legs of the bridge. By combining the two coils in the bridge configuration shown in FIG. 6, high signal gains can be applied to the detector which is nominally measuring a 'null' or zero voltage condition.

Figure 7:
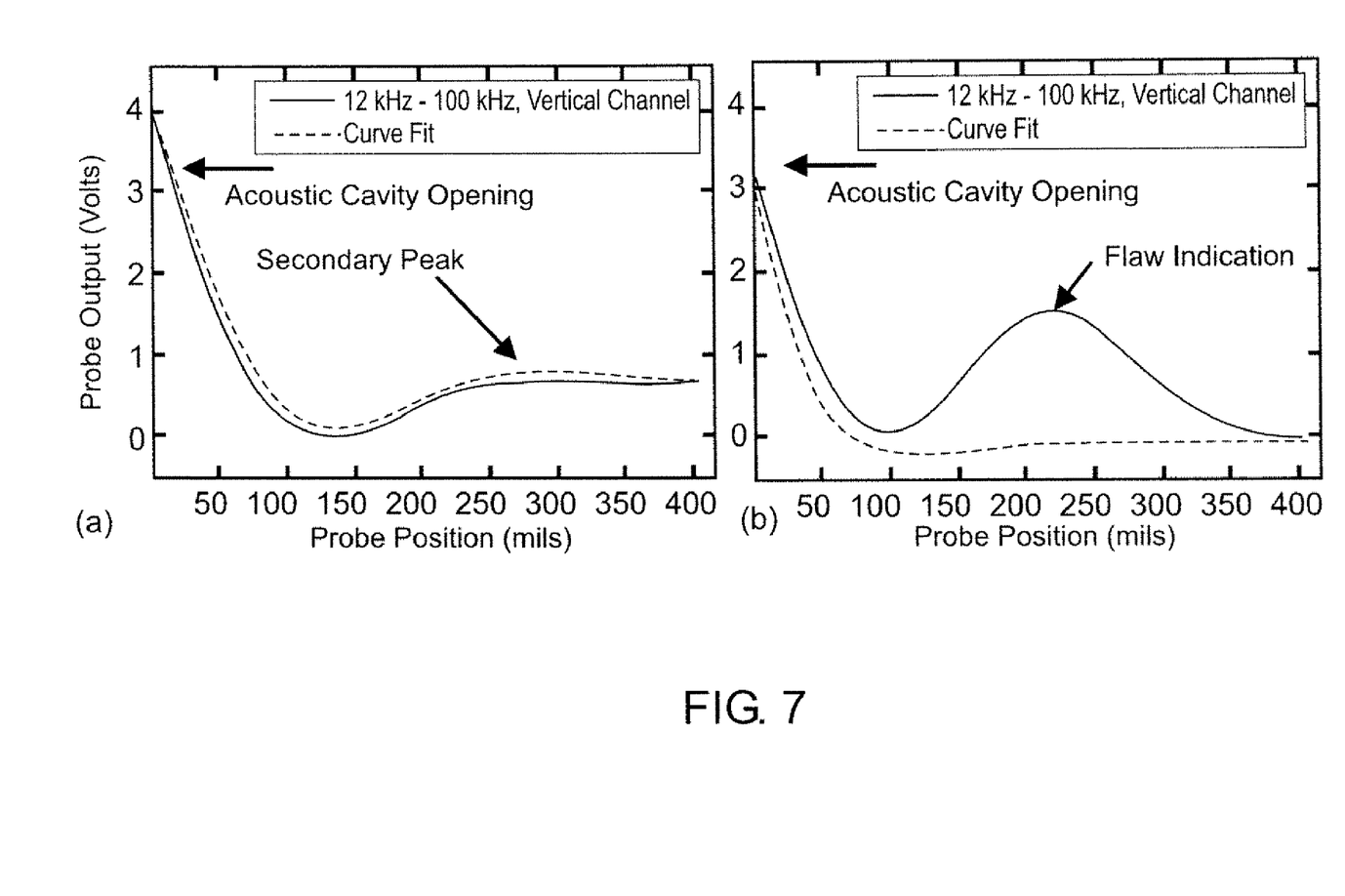
FIG. 7 illustrates the curve fitting procedure of a method for detecting sub-surface damage, in accordance with embodiments of the present invention.

Subtracting the high frequency vertical component from low frequency vertical component helps to remove other artifacts, such that subsequent analysis is performed on this difference signal. Analysis of this signal profile has led to a signal processing technique employing curve fitting to a cosine modulated exponential function. The vertical component of the low frequency probe response minus that of the high frequency is fit to a curve of the form $$V(x) = \cos(2\pi x/L) \times \exp(-x/A) \quad (2)$$

with L=the secondary peak location, x=scan position inside the cavity, and A=the curve fit parameter. The fit is also constrained to match the data at each end of the scan. FIG. 7 displays the results of applying this curve fitting procedure to an unflawed acoustic cavity (left plot) as well as a region where a notch approaches an acoustic cavity to within 0.040" remaining wall thickness (right plot). The difference between the raw data and the curve fit highlights the flawed region in the plot on the right. This technique is particularly useful for flaws growing at a steep angle, projecting to an intersection of the acoustic cavity near the cavity opening. It has been found that a calculation of the peak amplitude in the plot of the difference between the curve fit and the raw data correlates well with remaining wall thickness between the acoustic cavity and damage originating in the relief radius area. This calculated peak amplitude is the "Indication Strength" displayed by the system.

Based upon experimental data, a clear threshold can be established between unflawed thruster regions and areas with notches approaching to within 0.060" of the acoustic cavity wall. It should be noted that the experimental data corresponded to notches originating directly across from the acoustic cavity. As the eddy current coil is aligned in this direction, the sensor has maximum sensitivity for flaws in this orientation. As a part of the reference standard development, flaws originating at an off angle have also been fabricated. Test results have shown that the signal response for flaws originating between cavities as opposed to directly across from a cavity does drop, although flaws up to 0.060" away from the acoustic cavity are still typically detectable.

Naturally occurring stress corrosion cracking in PRCS thrusters has also been studied. The indication levels from this naturally occurring damage have been found to be as high or higher than those for simulated damage created using an electric discharge machine (EDM). The likely cause for the increased signal levels on naturally occurring damage is the flaw profile. All naturally occurring damage sites identified to date have shown a very high aspect ratio of crack length to crack depth. The notch standards were all fabricated with a two-to-one aspect ratio, and therefore likely underestimate the crack length at a given remaining wall thickness. The natural crack profile with a long circumferential direction also makes the occurrence of deep cracking between cavities with little damage directly across from the cavity unlikely. It therefore is reasonable to anticipate flaw detection capabilities for naturally occurring stress corrosion cracking to be at least as reliable as those for the calibration data.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

"Computer" or "computing device" broadly refers to any kind of device which receives input data, processes that data through computer instructions in a program, and generates output data. Such computer can be a hand-held device, laptop or notebook computer, desktop computer, minicomputer, mainframe, server, cell phone, personal digital assistant, other device, or any combination thereof.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Further discussion of the present invention is provided in Wincheski et al., Development of Eddy Current Techniques for the Detection of Cracking in Space Shuttle Primary Reaction Control Thrusters, NASA/TP-2007-214878, June 2007; Wincheski et al., Development of Eddy Current Techniques for the Detection of Stress Corrosion Cracking in Space Shuttle Primary Reaction Control Thrusters, Review of Progress in Quantitative NDE, Jul. 30-Aug. 4, 2006; and Wincheski, Validation Test Results for Orthogonal Probe Eddy Current Thruster Inspection System, NASA/TM-2007-215087, November 2007; the contents of each hereby incorporated by reference in their entirety.

What is claimed as new and desired to be secured by Letters Patent of the United States is:

1. A system for detecting damage below a surface of a cylindrical object, the system comprising:
    an eddy current probe comprising first and second eddy current coils, each coil being orthogonal to the other coil;
    a scanning mechanism to which the first and second eddy current coils are mounted, the scanning mechanism configured for moving the first and second eddy current coils in relation to the surface; and
    a dual frequency eddy current instrument configured for applying a current to the eddy current probe and measuring a resulting impedance as the eddy current probe is moved in relation to the surface; the dual frequency eddy current instrument further configured for either (1) concurrently applying a first current having a first frequency and a second current having a second frequency to the eddy current probe as the eddy current probe is moved in relation to the surface, or (2) alternatively applying a first current having a first frequency and a second current having a second frequency to the eddy current probe as the eddy current probe is moved in relation to the surface;
    wherein the first frequency is selected to penetrate the surface to a depth greater than or equal to a desired flaw detection depth, and the second frequency is selected to isolate a probe wobble and a surface effect, the second frequency being at least twice that of the first frequency;
    wherein the first eddy current coil comprises a first axis and the second eddy current coil comprises a second axis, and wherein the first and second eddy current coils are mounted to the scanning mechanism such that the first axis is aligned substantially with a circumferential direction of the surface as the eddy current probe is moved in relation to the surface, and such that the second axis is aligned substantially parallel to a longitudinal axis of the object as the eddy current probe is moved in relation to the surface, and wherein the first axis and the second axis do not intersect;
    wherein the scanning mechanism is further configured for varying a distance between the eddy current probe and the surface; and
    wherein the dual frequency eddy current instrument is further configured for rotating the measured impedance such that changes in the impedance caused by motion of the eddy current probe radially toward and away from the surface is along a predefined axis for both the first and second frequencies.

2. The system of claim 1, wherein the first frequency is between about 10 kilohertz and about 15 kilohertz, and wherein the second frequency is between about 90 kilohertz and about 110 kilohertz.

3. The system of claim 1, wherein the scanning mechanism comprises a stepper motor.

4. The system of claim 1, further comprising a display element for displaying the resulting impedance.

5. The system of claim 4, wherein the display element displays the resulting impedance at the first frequency, at the second frequency, and at a difference between the first and second frequencies.

6. The system of claim 1, further comprising a processing element configured for performing a curve fit of the measured impedance to a predefined function known to represent the measured impedance for an undamaged object.

7. The system of claim 6, wherein the predefined function is determined through experimental and/or simulation results and has a minimum number of fitting parameters.

8. The system of claim 6, wherein the processing element is further configured for calculating and monitoring an error between a best mathematical fit of the predefined function and the measured impedance as a determination of damage in the object.

9. A method for detecting damage below a surface of a cylindrical object, the method comprising:
providing an eddy current probe comprising first and second eddy current coils, each coil being orthogonal to the other coil, wherein the first eddy current coil comprises a first axis and the second eddy current coil comprises a second axis, and wherein the first axis and the second axis do not intersect;
moving the first and second eddy current coils in relation to the surface via a scanning mechanism to which the first and second eddy current coils are mounted;
applying a current to the eddy current probe via a dual frequency eddy current instrument; and
measuring a resulting impedance as the eddy current probe is moved in relation to the surface;
wherein a distance between the eddy current probe and the surface is varied and the measured impedance is rotated such that changes in the impedance caused by motion of the eddy current probe radially toward and away from the surface is along a predefined axis for both the first and second frequencies;
wherein applying a current to the eddy current probe via the dual frequency eddy current instrument comprises either (1) concurrently applying a first current having a first frequency and a second current having a second frequency to the eddy current probe as the eddy current probe is moved in relation to the surface, or (2) alternatively applying a first current having a first frequency and a second current having a second frequency to the eddy current probe as the eddy current probe is moved in relation to the surface;
wherein the first frequency is selected to penetrate the surface to a depth greater than or equal to a desired flaw detection depth, and the second frequency is selected to isolate a probe wobble and a surface effect, the second frequency being at least twice that of the first frequency; and
wherein the first and second eddy current coils are mounted to the scanning mechanism such that the first axis is aligned substantially with a circumferential direction of the surface as the eddy current probe is moved in relation to the surface, and such that the second axis is aligned substantially parallel to a longitudinal axis of the object as the eddy current probe is moved in relation to the surface.

10. The method of claim 9, wherein the first frequency is between about 10 kilohertz and about 15 kilohertz, and wherein the second frequency is between about 90 kilohertz and about 110 kilohertz.

11. The method of claim 9, wherein the scanning mechanism comprises a stepper motor.

12. The method of claim 9, wherein the method further comprises displaying the resulting impedance on a display element.

13. The method of claim 12, wherein displaying the resulting impedance on the display element comprises displaying the resulting impedance at the first frequency, at the second frequency, and at a difference between the first and second frequencies.

14. The method of claim 9, further comprising performing a curve fit of the measured impedance to a predefined function known to represent the measured impedance for an undamaged object.

15. The method of claim 14, wherein the predefined function is determined through experimental and/or simulation results and has a minimum number of fitting parameters.

16. The method of claim 14, further comprising:
calculating and monitoring an error between a best mathematical fit of the predefined function and the measured impedance as a determination of damage in the object.

* * * * *